(12) United States Patent
Tani et al.

(10) Patent No.: US 6,927,311 B2
(45) Date of Patent: Aug. 9, 2005

(54) METHOD FOR OXIDIZING CYCLOALKANE COMPOUND

(75) Inventors: Nobuhiro Tani, Ibaraki (JP); Shuzo Murata, Toyonaka (JP)

(73) Assignee: Sumitomo Chemical Company, Limited, Osaka (JP)

(*) Notice: Subject to any disclaimer, the term of this patent is extended or adjusted under 35 U.S.C. 154(b) by 88 days.

(21) Appl. No.: 10/396,832

(22) Filed: Mar. 26, 2003

(65) Prior Publication Data

US 2003/0216601 A1 Nov. 20, 2003

(30) Foreign Application Priority Data

Apr. 3, 2002 (JP) .......................................... 2002-101001

(51) Int. Cl.⁷ .............................................. C07C 35/08
(52) U.S. Cl. ...................... 568/836; 562/543; 568/821; 568/360
(58) Field of Search ................................ 568/821, 836, 568/360; 562/543

(56) References Cited

U.S. PATENT DOCUMENTS 2,223,494 A * 12/1940 Loder ........................ 568/360
3,351,657 A    11/1967 Herbert et al.
4,508,923 A     4/1985 Taylor et al.
5,728,890 A     3/1998 Hamamoto et al.
6,160,183 A    12/2000 Druliner et al.

FOREIGN PATENT DOCUMENTS

| EP | 0 063 931 A1 | 11/1982 |
| JP | 8-53379 A | 2/1996 |
| JP | 9-77704 A | 3/1997 |
| JP | 9-87215 A | 3/1997 |
| JP | 2000-319211 A | 11/2000 |
| WO | WO 99/40055 A1 | 8/1999 |

OTHER PUBLICATIONS

Derwent Publications Ltd., (XP002245929), Japanese Patent Application No. 9–77704, published Mar. 25, 1997.

* cited by examiner

*Primary Examiner*—Michael L. Shippen
(74) *Attorney, Agent, or Firm*—Sughrue Mion, PLLC

(57) ABSTRACT

A method for producing an oxygenated compound from a cycloalkane compound which method is characterized in that a cycloalkane compound is contacted with oxygen in the presence of a cobalt compound and a ruthenium compound.

17 Claims, No Drawings

METHOD FOR OXIDIZING CYCLOALKANE COMPOUND

FIELD OF THE INVENTION

The present invention relates to a method for oxidizing a cycloalkane compound.

BACKGROUND OF THE INVENTION

There have been disclosed in Japanese Patent Laid-Open No. 9-87215 (1997) a method for oxidizing cycloalkanes by allowing cycloalkanes to react with oxygen-containing gas in the presence of an imide compound and a ruthenium compound, and in WO9940055 a method of allowing cyclohexane to react under an oxygen atmosphere in the presence of the catalyst comprising the metallic compound supported on an inorganic compound carrier.

The method as disclosed in Japanese Patent Laid-Open No. 9-87215 (1997) uses an expensive imide catalyst and therefore is not satisfactory in cost. The method as disclosed in WO9940055 involves the step of preparing the solid catalyst and therefore is not efficient.

SUMMARY OF THE INVENTION

According to the present invention, oxygenated cycloalkane compound can be produced economically and efficiently.

The present invention provides: a method for producing an oxygenated compound from a cycloalkane compound, which comprises contacting a cycloalkane compound with oxygen in the presence of a cobalt compound and a ruthenium compound.

DETAILED DESCRIPTION OF THE INVENTION

The present invention is described in detail as follows.

Examples of the cycloalkane compound include, for example, cycloalkane and alkylcycloalkane such as cyclobutane, cyclopentane, cyclohexane, methylcyclohexane, cycloheptane, cyclooctane, cyclononane, cyclodecane or the like. Preferred is cyclohexane.

Typical examples of the cobalt compound include, for example, compounds of divalent or trivalent cobalt. Typical examples of the ruthenium compound include zero-valent, divalent, trivalent, or octavalent ruthenium compounds. Examples of the cobalt compound and the ruthenium compound include, for example, oxides, organic acid salts, inorganic acid salts, halides, alkoxides, complexes such as acetylacetonato complexes, oxo acids or salts thereof, isopolyacids or salts thereof, and heteropolyacids or salts thereof.

Preferred examples of the cobalt compound include, for example, cobalt acetate, cobalt octylate, cobalt naphthenate, cobalt stearate, cobalt acetylacetonato, cobalt chloride, and cobalt bromide. Preferred examples of the ruthenium compound include, for example, ruthenium acetylacetonato, triruthenium dodecacarbonyl, ruthenium oxide, ruthenium dioxide, and ruthenium chloride. Two or more of the cobalt compounds or the ruthenium compounds may be used in combination, if necessary.

Each of the cobalt compound and the ruthenium compound is usually used in an amount of 0.1 mol % or less, preferably 0.05 mol % or less, more preferably 0.01 mol % or less, per mol of the cycloalkane compound. The lower limit of the amount of the cobalt compound or the ruthenium compound is generally 0.000001 mol % or more, preferably 0.00001 mol % or more per mol of the cycloalkane compound.

The total amount of the cobalt compound and the ruthenium compound is preferably from 0.000001 to 0.1 mol %, more preferably from 0.00001 to 0.01 mol % per mol of the substrate cycloalkane compound.

The molar ratio of Co/Ru is generally 1/99 to 99/1, preferably 50/50 to 99/1, more preferably 80/20 to 99/1.

The reaction may be carried out in the presence of a solvent. Examples of the solvent include nitriles such as benzonitrile and acetonitrile; organic acids such as formic acid and acetic acid; organic nitro compounds such as nitromethane and nitrobenzene; and chlorinated hydrocarbons such as chlorobenzene and 1,2-dichloroethane, and a mixture thereof. Preferred examples thereof include, for example, the nitriles and the organic acids.

The solvent may be used per 100 parts by weight of the cycloalkane compound in an amount of generally 1 part by weight or more, preferably 10 parts by weight or more in terms of reaction velocity, and generally 80 parts by weight or less, preferably 50 parts by weight or less in terms of efficiency of the reactor volume.

Generally, the cycloalkane compound is contacted with oxygen, which is typically molecular oxygen, by bubbling of oxygen-containing gas into the reaction solution containing the cycloalkane compound, the cobalt compound, and the ruthenium compound. For example, such a process may be carried out using a gas introducing tube or blowing apertures provided in the inside of a reactor.

Examples of the oxygen-containing gas include oxygen, air, or a mixture gas in which oxygen or air is diluted with an inert gas such as nitrogen and helium. The oxygen-containing gas may be fed at a rate of generally 0.001 to 1 mole/hour in terms of oxygen, preferably 0.01 to 0.5 moles/hour in terms of oxygen, per 1 mole of the cycloalkane compound.

The reaction temperature is generally 70° C. or higher, preferably 90° C. or higher, more preferably 120 or higher in terms of reaction velocity, and generally 170° C. or lower, preferably 160° C. or lower. The reaction pressure is generally from 0.1 to 3 MPa, preferably from 0.5 to 2 MPa. The reaction may be carried out in a batch or continuous process. In terms of operability, the continuous process is preferred in which the cycloalkane compound, the cobalt compound, the ruthenium compound, and the oxygen-containing gas are fed into the reaction system while the reaction solution and the exhaust gas are withdrawn from the reaction system.

Examples of the oxygenated compound resulting from oxygenation of the cycloalkane compound include, for example, corresponding ketone, alcohol, hydroperoxide, aldehyde, and carboxylic acid compounds. Preferred are ketone, alcohol, hydroperoxide, and carboxylic acid compounds.

For example, a methylene group of the cycloalkane is converted into a carbonyl group, thereby corresponding ketone compound (cycloalkanone) is produced, or the methylene group is converted into a hydroxylated methylene group (—CH(OH)—), thereby corresponding alcohol compound(cycloalkanol) is produced, or it is converted into hydroperoxydated methylene group (—CH(OOH)—), thereby corresponding hydroperoxy compound is produced. Alternatively, a carbon-carbon bond of the cycloalkane is cleaved by further oxidation reaction of the carbonyl group or hydroperoxide group to produce corresponding dicarboxylic acid compound.

The alkylcycloalkane compound such as methylcycloalkane is usually oxidized so that the methylene group of the methylcycloalkane is typically converted into corresponding ketone, alcohol, hydroperoxide or dicarboxylic acid compound as above, moreover, the methyl group is oxidized and converted into corresponding alcohol compound having a hydroxylated methyl group (—CH$_2$OH), or corresponding hydroperoxide compound having hydroperoxydated methyl group (—CH$_2$OOH), or corresponding aldehyde compound having a formyl group (—CHO), or corresponding carboxylic acid compound having a carboxyl group (—COOH).

The oxidation process of the present invention may be conducted in the co-presence of the alcohol or ketone compound such as cycloalkanol or cycloalkanone compound resulting from the oxidation of the cycloalkane compound. In the oxidation process of the cycloalkane compound together with the cycloalkanol compound and/or cycloalkanone compound, the cycloalkanol and/or cycloalkanol compound are taken into account as the substrate to be oxidized.

Examples of the cycloalkanol compound include, for example, monohydric or polyhydric, cycloalkanols, which are derived from the cycloalkane compound and have a hydroxylated methyl group, a hydroxylated methylene group, or a hydroxylated tertiary carbon atom each derived from the methyl group, methylene group or the tertiary carbon atom of the cycloalkane compound.

For example, the cycloalkanol, which may be present together with the cycloalkane compound in the present oxidation process, is oxidized as follows.

The hydroxylated methylene group of the cycloalkanol is converted into a carbonyl group to produce corresponding ketone compound, which may be typically further oxidized to produce corresponding dicarboxylic acid by oxidative cleavage of a carbon-carbon bond of the cycloalkanol.

The hydroxylated methyl group of the cycloalkanol is converted into a formyl group to produce corresponding aldehyde compound, or further oxidized to a carboxyl group to produce a corresponding carboxylic acid.

The cycloalkanone compound is typically further oxidized and converted into corresponding dicarboxylic acid.

After completion of the reaction, concentration, washing, alkali treatment, acid treatment, and/or the like may be conducted. If necessary, two or more thereof may be carried out in combination. For example, the alkali treatment is carried out so that esters of alcohols and carboxylic acids that may be formed during the reaction can be saponified to give the alcohols and the carboxylic acids, and the hydroperoxides can be converted into ketones and/or alcohols. Distillation or crystallization is generally used to purify the desired product(s), if necessary.

The oxidizing method of the present invention typically provides at least one compound selected from the group consisting of ketone, alcohol, hydroperoxide, and carboxylic acid compound from the cycloalkane compound as a starting material and is preferably applied for producing the cycloalkanone and cycloalkanol compounds. The cycloalkanol as produced or separated can be recycled in the present oxidation process together with the cycloalkane compound. The cycloalkanol is typically oxidized in the present process to produce at least one compound selected from the group consisting of ketone and carboxylic acid compounds. Therefore, the more cycloalkanol compound is contained in the starting material, the more at least one compound selected from the group consisting of ketone and carboxylic acid compounds is produced as the product(s) in the present oxidation process.

For example, cyclohexane is used as the starting material to produce at least one compound selected from the group consisting of cyclohexanone, cyclohexanol, cyclohexyl hydroperoxide, and adipic acid. Cyclohexanol is typically converted to produce cyclohexanone and/or adipic acid.

In the oxidation of the cycloalkane compound, the cobalt compound and the ruthenium compound are used together to provide the desired products in a good yield. The concentration of the reaction intermediate hydroperoxide can be maintained at a lower range such as 1% or less. The method of the present invention is therefore industrially advantageous.

EXAMPLES

Examples of the present invention are described in the following, but such examples are not intended to limit the scope of the invention.

In the following examples, the oxygen-containing gas used was air or nitrogen-diluted air, which was blown through a gas introducing tube. The discharge of gas was carried out via a cooling pipe and a dwelling valve, and 8° C. water was used as the coolant in the cooling pipe. Cyclohexane, cyclohexanone, cyclohexanol, and cyclohexyl hydroperoxide were analyzed by gas chromatography, and adipic acid was analyzed by ion chromatography. Based on the results of the analysis, the reaction yields were calculated.

Example 1

To a 1-liter glass autoclave were added 252.6 g (3 moles) of cyclohexane, 0.00032 g (0.00000043 mole) of cobalt (II) octylate that contains 8 wt % of cobalt, 0.00010 g (0.00000025 mole) of ruthenium (III) acetylacetonato, 0.52 g (0.0053 mole) of cyclohexanone, and 0.52 g (0.0052 mole) of cyclohexanol and held at a temperature of 140° C. under a pressure of 1.05 MPa in a nitrogen atmosphere. With the temperature and the pressure maintained, the oxygen-containing gas with an oxygen concentration of 10% by volume was blown into the glass autoclave at a rate of 500 ml/minute for 1 hour. The oxygen-containing gas was then changed to air blowing at a rate of 250 ml/minute, and the flow rate was gradually increased to 500 ml/minute. When the oxygen-containing gas was changed to air, a solution containing cobalt (II) octylate at a concentration of 0.11 ppm by weight in terms of cobalt and ruthenium (III) acetylacetonato at a concentration of 0.11 ppm by weight in terms of ruthenium in cyclohexane was started to feed at a rate of 8.2 g/minute, and feeding of cyclohexane solution containing 3.1% by weight of cyclohexanone and 3.1% by weight of cyclohexanol was started at a rate of 0.75 g/minute at the same time. While maintaining the pressure and the temperature, the reaction solution was withdrawn at substantially the same rate as the feeding rate, and the reaction was carried out for 4 hours in a continuous process with a residence time of 0.5 hour. The discharged gas contained oxygen at an average concentration of 0.1% by volume. The whole amount of the supplied liquid contained cyclohexane at a concentration of 99 wt %, cyclohexanone at a concentration of 0.3 wt %, cyclohexanol at a concentration of 0.3 wt %, cobalt (II) octylate at a concentration of 0.10 ppm by weight in terms of cobalt, and ruthenium (III) acetylacetonato at a concentration of 0.10 ppm by weight in terms of ruthenium.

The analysis of the reaction solution revealed to contain cyclohexanone at a concentration of 2.1 wt %, cyclohexanol at a concentration of 1.9 wt %, and cyclohexyl hydroperoxide at a concentration of 0.2 wt %.

The conversion rate of cyclohexane was 4.0%, and the total yield of cyclohexanone, cyclohexanol, and cyclohexyl hydroperoxide was 3.2% (selectivity 80.2%).

Example 2

To a 1-liter glass autoclave were added 253.0 g (3 moles) of cyclohexane, 0.00032 g (0.00000043 mole) of cobalt (II) octylate containing cobalt 8 wt %, 0.00010 g (0.00000025 mole) of ruthenium (III) acetylacetonato, 0.54 g (0.0055 mol) of cyclohexanone, and 0.56 g (0.0056 mol) of cyclohexanol and held at a temperature of 14° C. under a pressure of 1.05 MPa in a nitrogen atmosphere. While maintianing the temperature and the pressure, the oxygen-containing gas with an oxygen concentration of 10% by volume was blown into the glass autoclave at a rate of 400 ml/minute for 1 hour. The oxygen-containing gas was then changed to air and air was blown at a rate of 250 ml/minute, and the flow rate was gradually increased to 275 ml/minute. When the gas was changed to air, feeding of cyclohexane containing cobalt (II) octylate at a concentration of 0.10 ppm by weight in terms of cobalt and ruthenium (III) acetylacetonato at a concentration of 0.10 ppm by weight in terms of ruthenium, cyclohexane containing 0.2 wt % of cyclohexanone and 0.2 wt % of cyclohexanol at a rate of 4.5 g/minute was started. With the pressure and the temperature maintained, the reaction solution was withdrawn at almost the same rate as the feeding rate, and the reaction was carried out for 6 hours in a continuous process with a residence time of 1.0 hour. The discharged gas contained oxygen at an average concentration of not more than 0.1% by volume. Analysis of the reaction solution showed that it contained cyclohexanone at a concentration of 2.3% by weight, cyclohexanol at a concentration of 1.5 wt %, and cyclohexylhydroperoxide at a concentration of 0.5 wt %.

The conversion rate of cyclohexane was 4.1%, and the total yield of cyclohexanone, cyclohexanol, and cyclohexyl hydroperoxide was 3.3% (selectivity 81.4%).

Examples 3 to 7

In Example 3, the experiment was conducted in a similar manner as in Example 2 except that 0.00057 g (0.00000078 mol) of cobalt (II) octylate with a cobalt content of 8 wt %, and 0.000020 g (0.000000050 mol) of ruthenium (II) acetylacetonato, were used and the cobalt content and the ruthenium content were 0.18 ppm and 0.02 ppm. In Examples 4 to 7 the experiments were conducted in a similar manner as in Example 2 except that ruthenium compounds as listed in Table 1 were used in place of ruthenium (II) acetylactonato.

TABLE 1

| Example | Ruthenium compound | A/B/C (wt %) | Conv. (%) | Yield (%) | Select (%) |
| --- | --- | --- | --- | --- | --- |
| 3 | — | 2.2/1.5/0.5 | 3.9 | 3.2 | 82.8 |
| 4 | Ruthenium octylate | 2.2/1.7/0.4 | 4.1 | 3.3 | 81.2 |
| 5 | Ruthenium chloride | 2.1/1.9/0.3 | 4.1 | 3.3 | 81.5 |
| 6 | Bis (isoheptadionato) - norbornadiene ruthenium | 2.2/1.6/0.3 | 3.9 | 3.2 | 81.9 |
| 7 | Ruthenocene | 2.2/1.6/0.4 | 4.0 | 3.2 | 81.4 |

TABLE 1-continued

| Example | Ruthenium compound | A/B/C (wt %) | Conv. (%) | Yield (%) | Select (%) |
| --- | --- | --- | --- | --- | --- |

A/B/C: Wt % concentration of cyclohexanone, cyclohexanol, and cyclohexylhydroperoxide respectively.
Conv.: conversion ratio of cyclohexane.
Yield: Total yield of Cyclohexanone, Cyclohexanol and Cyclohexylhydroperoxide.

What is claimed is:

1. A method for producing an oxygenated compound from a cycloalkane compound, consisting essentially of contacting a cycloalkane compound with oxygen in the presence of a cobalt compound and a ruthenium compound.

2. The method according to claim 1, wherein molar ratio between Co and Ru is 1:99 to 99:1.

3. The method according to claim 1, wherein molar ratio between Co and Ru is 50:50 to 99:1.

4. The method according to claim 1, wherein molar ratio between Co and Ru is 80:20 to 99:1.

5. The method according to claim 1 or 2, wherein the cobalt compound and the ruthenium compound are used in a total amount of 0.000001 to 0.1 mol % per mol of the cycloalkane compound.

6. The method according to claim 1 or 2, wherein the cobalt compound and the ruthenium compound are used in a total amount of 0.00001 to 0.01 mol % per mol of the cycloalkane compound.

7. The method according to any one of claims 1, 2 and 3, wherein the oxygenated compound is at least one compound selected from the group consisting of corresponding ketone, alcohol, hydroperoxide and carboxylic acid compounds.

8. The method according to claim 1, wherein the contacting of the cycloalkane compound with oxygen is conducted at a temperature range of 70to 170° C.

9. The method according to claim 1, wherein the contacting of the cycloalkane compound with oxygen is conducted at a temperature range of 120 to 160° C.

10. The method according to claim 1, wherein the cycloalkane compound is cycloalkane.

11. The method according to claim 1, wherein a cycloalkanol compound is present in the cycloalkane compound.

12. The method according to claim 10 or 11, wherein a cycloalkanone compound is present in the cycloalkane compound.

13. The method according to claim 1, 2, 3, or 4, wherein the cycloalkane compound is cyclohexane.

14. The method according to claim 11, wherein the cycloalkane compound is cyclohexane and the cycloalkanol is cyclohexanol.

15. The method according to claim 12, wherein the cycloalkane compound is cyclohexane, the cycloalkanol is cyclohexanol, and the cycloalkanone is cyclohexanone.

16. The method according to claim 1, wherein the ruthenium compound is selected from the group consisting of ruthenium acetylacetonate, triruthenium dodecacarbonyl, ruthenium oxide, ruthenium dioxide, ruthenium octylate and ruthenium chloride.

17. A method according to claim 1, wherein the cobalt compound is selected from the group consisting of cobalt acetate, cobalt octylate, cobalt naphthenate, cobalt acetylacetonate, cobalt chloride and cobalt bromide.

* * * * *